United States Patent [19]
Denkewalter et al.

[11] 4,289,872
[45] Sep. 15, 1981

[54] MACROMOLECULAR HIGHLY BRANCHED HOMOGENEOUS COMPOUND BASED ON LYSINE UNITS

[75] Inventors: Robert G. Denkewalter, Westfield; Jaroslav Kolc, Randolph Twp., Morris County; William J. Lukasavage, Harrison, all of N.J.

[73] Assignee: Allied Corporation, Morris Township, Morris County, N.J.

[21] Appl. No.: 27,622

[22] Filed: Apr. 6, 1979

[51] Int. Cl.³ .............................................. C08G 69/10
[52] U.S. Cl. .................................... 528/328; 528/310
[58] Field of Search ................................ 528/328, 310

[56] References Cited
U.S. PATENT DOCUMENTS 4,132,746  1/1979  Urry et al. ........................... 528/328

Primary Examiner—Harold D. Anderson
Attorney, Agent, or Firm—Robert A. Harman

[57] ABSTRACT

Formed from trifunctional units (M) having attached, to one of two terminal carbon atoms of an alkylene hydrocarbon diradical, the functional group A', and having attached, to the other terminal carbon atom, a different functional group B' reactive with A' to form a linkage AB; and having attached, to a third carbon of the skeleton of unit (M), the functional group A" (preferably the same as A') reactive with B' whereby a macromolecule is built up of successive layers of units (M). The process involves successive stages in the first of which, the functional groups A' are blocked and group B is blocked with a "source" unit (S); then groups A' are liberated to form Compound I. In the second stage, Compound II is formed from the starting material (such as lysine) by first blocking groups A', then converting group B' to a form reactive with A'. Then a series of growth steps links two molecules of Compound II to each molecule of Compound I via reaction between activated B' groups of two Compound II molecules, and two liberated A' groups of Compound I; and the four blocked groups A' in the two newly added units are liberated to form Compound III. In stage C, the four A' groups of Compound III are reacted as before with Compound II, and the eight blocked A' groups of the resultant newly added units (M) are liberated to complete the third stage; and so on. Lysine is illustrative of suitable starting materials. The products can be used as surface modifying agents; as metal chelating agents; and as substrates for preparation of pharmaceutical dosages.

5 Claims, 1 Drawing Figure

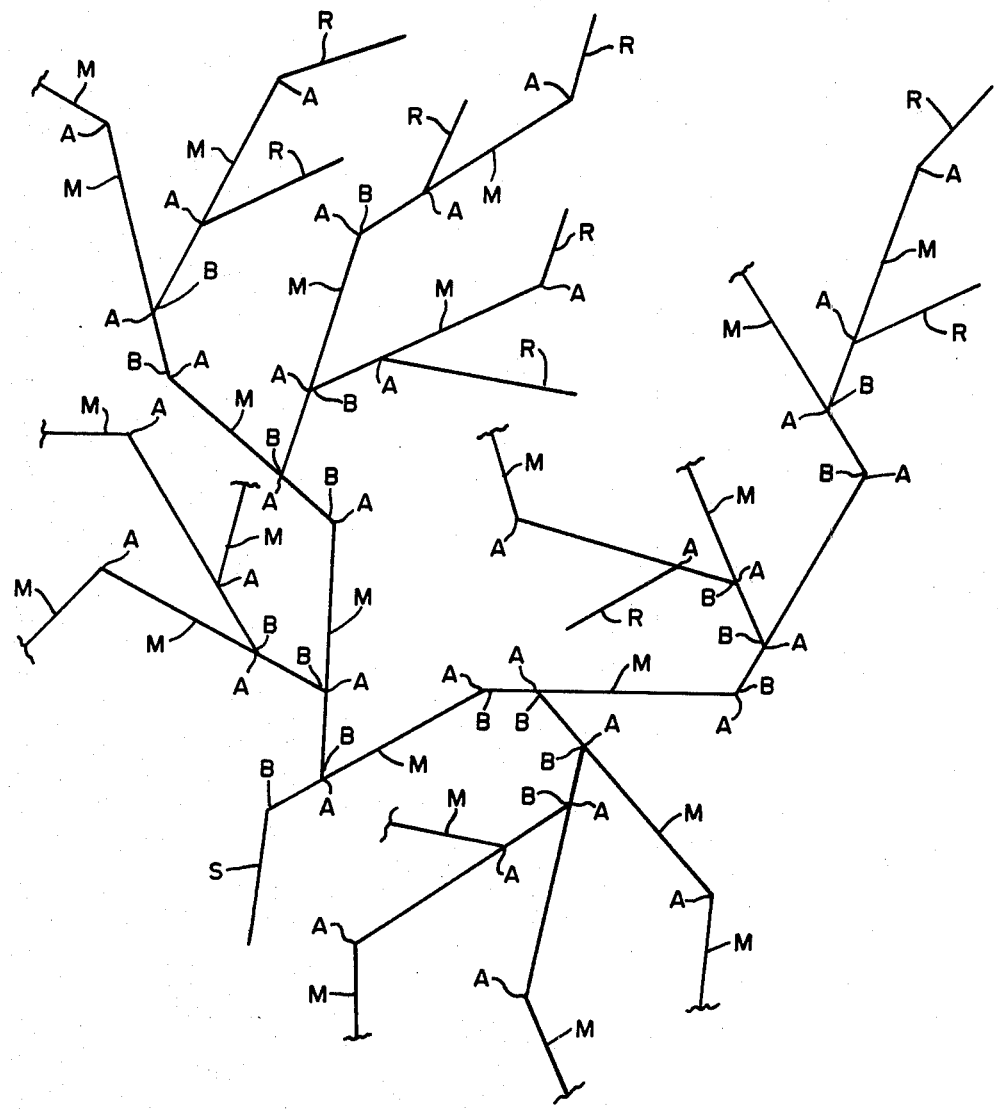

MACROMOLECULAR HIGHLY BRANCHED HOMOGENEOUS COMPOUND BASED ON LYSINE UNITS

DESCRIPTION

This invention relates to organic macromolecular compounds, i.e. compounds in which essentially all constituent molecules are alike in composition, chemical structure and size (see *J. Pol. Sci.*, volume VIII, No. 3—"Report on Nomenclature in the Field of Macromolecules"—pages 257-277 at page 258). These compounds are to be distinguished from high polymers wherein the composition is a mixture of homologous polymeric compounds. The subject compounds are branched but not crosslinked and are composed essentially of identical trifunctional units.

High polymers, consisting of a mixture of homologous polymeric compounds, composed of trifunctional units, are well known, in particular in the form of naturally occurring proteins and related natural and synthetic materials. For example, linear polymeric lysine is known in which one of the two amino groups in one lysine unit is combined with a carboxyl group of another lysine unit, to form a chain of lysine units linked by amide (—NHCO—) linkages.

SUMMARY OF THE INVENTION

The compounds of this invention differ from prior art high polymers in that each constituent unit of the macromolecular compounds of this invention can be characterized as being an interior unit, an exterior unit, the source unit, or permissibly a surface unit. Each interior unit (M) consists of an alkylene hydrocarbon diradical of at least 3 carbon atoms having attached, to one of the two terminal carbon atoms of such diradical, the residue "A" of one functional group, and having attached to the other terminal carbon atom of such diradical, the residue "B" of a different functional group capable of reacting with the first group. Thus, in these macromolecular compounds, the interior units (M) are linked one to another by a linkage AB. Also attached to each such interior unit (M) at a third carbon atom in its skeleton, is a residue of a functional group which generally will be a residue A, serving to link said interior unit (M) to a third like unit, via said residue A and the residue B attached to a carbon atom of said unit (M).

The above mentioned exterior units of the subject macromolecules having a similar structure (M) to that of the interior units and are linked to interior units also by linkages AB. In each such exterior unit, at least one of its two residues A is part of an original unreacted functional group; or forms a linkage between such exterior unit, and a surface unit (R) different from the said units (M). Said macromolecules contain additionally, one source unit (S) having at least one residue therein linking the unit (S) by a linkage SB to an interior unit (M) only via one or more linkages of (S) with the residue B attached to a carbon atom of unit (M); source unit (S) being otherwise unreacted with units (M). Thereby the total number of units (M), interior and exterior, in the subject macromolecules closely approximates $(2^n - 1)$ with "n" being at least 4; and additionally, the macromolecule contains one source unit (S). In this expression "n" is the number of successive layers of units (M) added onto the source unit (S).

A process for producing such macromolecule involves an initiation stage wherein source units (S) are combined with one or more units (M) of the ultimate macromolecule; followed by a series of growth stages, in each of which a set of growth steps is carried out, until a stage is reached at which the desired molecular weight of the macromolecule has been attained.

BRIEF DESCRIPTION OF THE DRAWING

The single FIGURE of the drawing is a two dimensional diagrammatic representation of the structure of the macromolecules of high polymeric compounds of the invention. In the drawing, the straight lines represent the monomeric units of the macromolecules and the angles represent linkages between these monomeric units. The letter S in the drawing designates the "source" unit of the illustrated macromolecule; the letters M designate representative interior and exterior units; and the letters R designate representative surface units different from the M's.

DESCRIPTION OF PREFERRED EMBODIMENTS

In preferred embodiments of the invention, the source unit (S) is linked to one interior unit (M) or to two or even more such units, only via linkages involving the residue "B" of the unit (M). Moreover, when the exterior units are linked in turn to units (R) different from the units (M), the units (R) have thereon a terminal group different from the functional group from which the residue A of the units (M) is obtained. This different terminal group can suitably be hydroxyl, carboxy, guanidino, cyano, isocyanato, mercapto, sulfo or other desired functional group, the same in all the (R) units or different in different (R) units; or the (R) units can be inert, e.g. fluorinated.

The compound lysine, i.e. 2,6-diaminocaproic acid, is representative of compounds which can be used to supply the trifunctional units (M) basically composing our macromolecules. It will be noted that in lysine, the functional groups which provide the above designated residue A are both the same, being amino groups. It is not absolutely necessary that the functional groups be the same, or even that the residue A be the same at each occurrence, but such structure is convenient since a linkage is to be formed from each of two residues A in one molecule and the third residue B in another molecule. When the units (M) are derived from lysine, the unit (R) different from the principal units (M) will be derived from a molecule having at least one group reactive with the amino group, such as an anhydride, acid halide, or isocyanato group.

The process of producing the macromolecular compounds of this invention comprises an initiation stage (A), followed by a series of growth stages in each of which a set of growth steps is carried out; the set is repeated until the desired molecular weight of the macromolecule is obtained.

Thereafter, if desired, an additional stage can be had in which surface units R, different from the units (M) used initially, can be added to the exterior units (M) composing the surface of the basic macrmolecule of the invention.

(A) More specifically our process, illustrated with reference to lysine as the basic constituent of the macromolecules of the invention, comprises combining "source" units, one each, with lysine units in an initiation stage involving;

(1) Blocking the two amino groups of lysine molecules by conversion thereof to urethane groups;

(2) Blocking the carboxyl group of the obtained diurethane of lysine by linking of the lysine carboxyl group with the "source" unit thus producing a derivative of lysine (such as an N-substituted amide) at said carboxyl group, inert toward amino groups, which derivative contains a first lysine unit (M) and a "source" unit (S);

(3) Liberating the two amino groups of such first lysine units (M) by hydrolysis of the two urethane groups, thus obtaining Compound (I), the formula of which is symbolized below as Lys(S);

(B) As the second stage, our process begins growth, linking two more lysine units (M) to each of the first lysine units (M) by steps involving:

(1) Blocking the two amino groups of lysine as in step (A)(1) above by conversion of each to a urethane group;

(2) Converting the carboxyl group of the diurethano lysine, obtained in step (B)(1) above, to a carboxyl derivative reactive with amino groups, such as anhydride, para-nitrophenyl ester, or carboxy chloride; thereby forming Compound II;

(3) Contacting the diamino-containing Compound (I), obtained as in step (A)(3) above, with the reactive carboxyl derivative, Compound (II) of step (B)(2) above, to form amide linkages —CONH— and thereby link the lysine unit (M) of compound I via its two amino groups to each of two diurethano lysine units (M) of Compound II via their carboxyl groups; and then liberating four amino groups by hydrolysis of the four newly added urethane groups, thereby forming Compound III, i.e. Lys Lys(S);

(C) As a third stage repeating the steps of blocking lysine amino groups; converting the carboxyls of the resulting diurethano lysines to a reactive derivative, i.e. Compound II; linking four of these Compound II molecules, via their reactive carboxyl derivative, to the four amino groups in each molecule of Compound III; and then liberating the eight amino groups of the four newly added lysine units to form Compound IV;

(D) Repeating as desired the set of growth steps of stage (C) above, thereby at each new stage increasing by a factor of essentially 2, the number of lysine units contained in the resulting macromolecule.

It will be recognized that after each successive growth stage, the most recently added lysine units are "exterior" units; and when the next further growth stage is carried out, these exterior units now become additional "interior" units.

Since the total number of exterior units added at each growth stage is double the number of exterior units present at the end of the preceding stage, the total number of units (U) of lysine in the basic macromolecule will be $U = 1 + 2 + 2^2 + 2^3 + \ldots + 2^{n-1}$ after formation of Compound I followed by $(n-1)$ growth stages, or $U = 2^n - 1$. Of these lysine units (M), one is linked via its carboxyl group to the source unit (S); the outermost layer, or $2^{(n-1)}$ units, are exterior units (M); and the remainder are interior units (M).

If desired, as above-indicated, the basic macromolecule of lysine units can be modified by the further process step of reacting some or all of the free amino groups of the exterior units with functional groups of one or more modifying species (R), (R'), ... to add surface units different from the lysine units. For example these (R's) can be derived from aminoacids different from lysine, such as phenylalanine and tyrosine; or can be derived from cyclic anhydrides whereby surface units (R) are linked by amide linkages (—NHCO—) to the exterior lysine units (M) of the basic macromolecule, and these units (R) carry a free carboxyl group as formed by reaction of the cyclic anhydride with the amino groups. Also the surface units (R) can be derived from a compound containing reactive halogen, such as bromoacetic acid, whereby the unit (R) is carboxymethyl of formula —CH₂COOH. Carboxyl groups in such surface units can be partially or fully neutralized to the form of a salt, e.g. sodium salt. Another alternative is to introduce particular (R) units, such as fluorinated (R), aromatic (R) or heterocyclic (R) derived from compounds having a group reactive with amino groups, such as an acid halide group. A further alternative is the complexing of amino and/or carboxy groups, at the surface of the macromolecule, with metallic compounds.

Numerous other possibilities of linking various compounds, via reactive substituent groups, with the lysine amino groups, for various purposes, will be readily apparent to those skilled in the art of organic chemistry. Moreover, as another alternative for providing "R" units, free amino groups of lysine can be converted to different groups. For example, such amino groups can be converted by action of phosgene to isocyanate groups; and if desired, these isocyanate groups can be brought into reaction with suitable substituents on organic compounds, such as —OH, —NH₂, etc. to provide units (R).

Utility for compounds of the invention is as surface modifiers for any surface toward which these compounds are substantive e.g. surfaces capable of hydrogen bonding with the free amino groups of the above lysine macromolecules; as metal chelating agents via their free groups such as amino and/or carboxy; as substrates for preparation of pharmaceutical dosages; and the like.

The following specific example is illustrative of our invention and of the best mode presently contemplated by us for carrying out the invention. In the example, the special abbreviations used are as follows:

BHA = Benzhydrylamine (formula Ph₂CHNH₂). Used to form a "source" unit by blocking the carboxyl group of lysine by formation of the (—CONHCHPh₂) amide group.

DBC = Di(t-butyl)dicarbonate (commercially available).

DBL = N,N'-Di(t-butyloxycarbonyl)lysine. L-Lysine with the two amino groups blocked by formation of (t—C₄H₉OCONH—) urethane groups. (Commercially available).

DBL-PNE = Para-nitrophenyl ester of DBL. To convert DBL carboxyl group to reactive derivative.

DCC = Dicyclohexylcarbodiimide (formula (C₆H₁₁)N=C=N(C₆H₁₁)). Used to remove the elements of water from carboxyl groups of lysine, forming the anhydride (reactive with amino, hydroxyl and like groups) and dicyclohexylurea coproduct.

Lys = L-Lysine.

TFA = Trifluoroacetic acid. F₃CCOOH. Used to reconvert urethane groups to amino groups.

In summary outline, the procedure described in detail below can be formulated as follows:

Stage (A)

| -continued | |
|---|---|
| (1) Lys + DBC | DBL (Diurethane of Lysine) |
| (2) DBL + DCC + BHA | Amide (DBL)(BHA) |
| (3) (DBL)(BHA) + TFA | Diamino form of Lys (BHA), i.e. Cmpd I (crystallized as dihydrochloride) |
| Stage (B) | |
| (1) Same as (A)(1) | DBL |
| (2) DBL + DCC + p-nitrophenol | DBL-PNE, i.e. Cmpd II |
| (3) 2 Cmpd II + Cmpd I | Diamide, $(DBL)_2$ Lys(BHA) |
| (4) $(DBL)_2(Lys)(BHA)$ + TFA | Tetramine, $Lys_2$ Lys (BHA), i.e. Cmpd. III |
| Stage (C) | |
| (1) Same as (B)(1) | DBL |
| (2) Same as (B)(2) | DBL-PNE, i.e. Cmpd II |
| (3) 4 Cmpd II + Cmpd III | Tetramide, $(DBL)_4Lys_2Lys$ (BHA) |
| (4) Tetramide + TFA | Octamine, $Lys_4Lys_2Lys(BHA)$, i.e. Cmpd IV. |

Subsequent stages utilize the same procedure in principle.

STAGE A—Preparation of Lys (BHA)=Compound I

Step 1: DBL can be obtained from lysine as indicated at stage (A)(1) in the above outline; it was purchased.

Step 2: A sample of 10 grams (28.9 mmoles) of DBL was dissolved and brought to 25 ml volume in $CH_2Cl_2$. To this were added 5.3 grams (28.9 mmoles) BHA followed by 11.93 grams (57.8 mmoles) DCC and the volume quickly adjusted to 75 ml with additional $CH_2Cl_2$. Because of a moderate exotherm an ice water bath was employed for a few minutes to avoid bumping of the volatile $CH_2Cl_2$ (b.p. 40° C.).

After one hour the resulting dicyclohexylurea precipitate was filtered off and the cake washed twice with 10 ml portions of $CH_2Cl_2$. The filtrate, containing dissolved DBL amide of BHA, was allowed to stand another half hour to observe whether additional urea precipitation occurred. This did not happen and the reaction was considered complete. The filter cake was then dispersed in $CH_2Cl_2$ and mixed with TFA to note any evolution of $CO_2$ gas as a spot check for occluded product or unreacted DBL in the filter cake. (The acid will decompose the t-butyloxy urethane groups of any occluded DBL(BHA) or unreacted DBL, with formation of $CO_2$). No bubbles were observed.

The initial filtrate containing DBL(BHA) was then extracted twice with 25 ml portions of water made basic with NaOH to remove unreacted DBL. The filtrate was then dried over about two grams of anhydrous sodium sulfate. The resulting crystal clear amber solution was filtered and the sodium sulfate cake washed twice with 10 ml portions of $CH_2Cl_2$. The volume of the filtrate plus washings was reduced to about 25 ml and brought back to 75 ml with TFA to liberate the blocked amino groups, thus decomposing the t-butyloxycarbonyl groups to butanol and carbon dioxide and forming Compound I. After about two hours, well after cessation of $CO_2$ bubbling, the volume of the solution was reduced as far as possible by heating in a 50° C. water bath while blowing with $N_2$. The resulting oil was then brought to about 100 ml volume with $CH_3CN$; and this solution was mixed with an excess of HCl dissolved from the gas in EtOH; then was mixed with additional $CH_3CN$ unttil the resulting product, Compound I (as hydrochloride), commenced to crystallize. After about one hour, additional $CH_3CN$ was added. As this did not induce further crystallization a thin layer chromatograph was run and showed very little product remaining in solution.

Initial yield of the crystallized product, Compound I (as hydrochloride of the diamine) was about 6.75 grams (61% based upon DBL). The product was recrystallized for further purification by first dissolving in a minimum quantity of 90% $EtOH/H_2O$, then precipitating with $CH_3CN$.

STAGE (B)—$(Lys)_2Lys$ (BHA)=Compound III

A sample of 2.72 grams of the Compound I (as hydrochloride ) was added to 15 ml of dimethylformamide (DMF) and converted to the free amino form by bringing to pH 7–9 with about 1 ml of triethylamine. To this DMF solution, containing the free amino form of Compound I, was added 13.1 grams of Compound II, N,N'-di(t-butyloxycarbonyl) lysine p-nitrophenyl ester (DBL-PNE), obtained by reaction of DBL with DCC and p-nitrophenol essentially by the procedure of Step (A)(2) above. The resulting solution was maintained at pH 8–9 by dropwise addition of triethylamine, and the reaction was monitored of Compound I with Compound II by tlc (thin layer chromatography); it appeared complete both by the tlc analysis and by stability of the pH, at the end of 2½ hours. The resulting solution of N,N'-$(DBL)_2Lys$ (BHA) was added to 500 ml of water and was stirred overnight. The precipitate was filtered and washed with water and dried in vacuo at about 40° C. The dry precipitate was washed with 300 ml of diethyl ether and successively with 150 ml portions of diethyl ether until the ether showed no yellow color on treatment with aqueous sodium hydroxide. At this point the cake was essentially colorless. The product, $(DBL)_2$ Lys (BHA), was dried in vacuo at about 40° C. Yield: 6.13 grams (90% of theory).

A sample of 5.8 grams of this product, $(DBL)_2$ Lys (BHA) was added to a mixture of 30 ml of trifluoroacetic acid (TFA) and 30 ml of methylene chloride in a 3-neck flask fitted with a stirrer and a gas collection trap. The amount of $CO_2$ liberated was determined by sweeping the exit gases with nitrogen through a solution of barium hydroxide. The reaction liberated the amino groups, forming Compound III. It was judged complete at the end of an hour; weighing of the dried barium carbonate precipitate indicated essentially 100% evolution of $CO_2$.

STAGE C—$(Lys)_4Lys_2Lys$ (BHA)=Compound IV

The solution of Compound III from Stage B was evaporated to a thick oil in a 50° C. water bath with a nitrogen sweep. To this was added 25 ml of dimethylformamide (DMF) and the pH adjusted with triethylamine to 7–8 using 13 ml of triethylamine. To this solution was added 23 grams of DBL-PNE, i.e. Compound II, and the reaction of Compound II with the free amino groups of Compound III was allowed to proceed for 40 hours with periodic pH adjustment with triethylamine to maintain the pH above 8; its course was monitored by thin layer chromatography. The reaction solution was then precipitated in 800 ml of water and washed twice with 300 ml of water. The precipitate, $(DBL)_4Lys_2$-Lys(BHA) was dried in vacuo at 40° C. and washed with 600 ml diethyl ether and successive 300 ml portions of diethyl ether; then was dried in vacuo at 40° C. Yield: 11.3 grams (100% of theory).

A sample of 9.4 grams of this $(DBL)_4Lys_2Lys(BHA)$ was added to a mixture of 50 ml of TFA and 50 ml of methylene chloride, which was stirred for 70 minutes to liberate the amino groups, forming the octamine, Compound IV, in solution. $CO_2$ evolution was judged complete.

STAGE D—$Lys_8Lys_4Lys_2Lys(BHA)$=Compound V

The solution of compound IV was evaporated in a 50° water bath to remove excess methylene chloride and TFA. The residue, Compound IV, remained as a thick oil to which was added 35 ml of DMF. The pH was adjusted to 8.9-9.3 with triethylamine, then 37.2 grams of DBL-PNE, i.e. Compound II, was added. The reaction was allowed to proceed for approximately 36 hours, with periodic pH adjustment with triethylamine to maintain the pH above 8, and with analysis by tlc to monitor the course of the reaction. The reaction solution was then precipitated in about 1 liter of water and washed with two 400 ml portions of water. Precipitate was dried in vacuo at 40° C. and washed with 700 ml of diethyl ether and successive 400 ml portions of diethyl ether until the ether wash showed no yellow color with aqueous sodium hydroxide. The product $(DBL)_8Lys_4Lys_2Lys(BHA)$ was dried in vacuo at 40° C. Yield: 14.5 grams (78.4% of theory).

A sample of 5.0 grams of the $(DBL)_8$ product was added to a mixture of 14 ml methylene chloride and 27 ml TFA, which was stirred for two hours at room temperature to liberate the amino groups. The solution of $Lys_8Lys_4Lys_2Lys(BHA)$ (Compound V) was then evaporated to remove excess methylene chloride and TFA.

STAGE E—$Lys_{16}Lys_8Lys_4Lys_2Lys(BHA)$=Compound VI

To the remaining oil was added 20.5 ml of DMF and the solution was neutralized to about pH 10 with triethylamine. 17.14 grams of DBL-PNE, i.e. Compound II, was added and the solution was stirred for 24 hours with periodic pH adjustment with triethylamine to maintain the pH above 8. The solution was added to 1400 ml of water and was stirred over the weekend. An additional 1 liter of water was then added. After a period of stirring the mixture was filtered. The cake was washed with water and dried in vacuo at 40° C. The dry precipitate, $(DBL)_{16}Lys_8Lys_4Lys_2Lys(BHA)$, was washed with 600 ml of diethyl ether and then with two 600 ml portions of acetonitrile. The product was filtered and dried in vacuo at 40° C. Yield: 8.53 grams (85% of theory).

A sample of 1.83 grams of the $(DBL)_{16}$ product was added to a mixture of 5 ml of methylene chloride and 10 ml of TFA in a flask with a gas absorption train. The amount of $CO_2$ liberated was estimated at 94% of theory based on barium carbonate generated over a two hour period. The solution of $Lys_{16}Lys_8Lys_4Lys_2(BHA)$, Compound VI, was then evaporated to remove excess methylene chloride and TFA.

STAGE F—$Lys_{32}(Lys)_{31}(BHA)$=Compound VII

The oil was diluted with 7½ ml of DMF and neutralized with triethylamine to pH of about 8.5. To this solution was added 7.44 grams of DBL-PNE, i.e. Compound II. The solution was stirred for 26 hours while the pH was maintained between 8-9 by addition of triethylamine. The solution was then added to 300 ml of water. After a settling period the water was decanted; then an additional 300 ml of water was added and the mixture was stirred over the weekend. The mixture was filtered and the cake dried in vacuo at 40° C. and washed with 300 ml of diethyl ether and then with four successive portions of 100 ml each of diethyl ether. Yield of $(DBL)_{32}(Lys)_{31}(BHA)$ 3.46 grams (94.4% of theory).

A sample of 2.0 grams of the $(DBL)_{32}$ product was added to a mixture of 8 ml methylene chloride and 20 ml TFA. The gas evolved during a two hour period was bubbled through a barium hydroxide trap, and the $CO_2$ liberated was estimated at 92% of theory based on barium carbonate recovery. The solution of $Lys_{32}(Lys)_{31}(BHA)$, Compound VII, was then evaporated to remove excess TFA and methylene chloride.

STAGE G—$Lys_{64}(Lys)_{63}(BHA)$=Compound VIII

To the resulting amino product, 7.5 ml of DMF was added. The pH was adjusted to about 8 with triethylamine, and there was added 8.19 grams of DBL-PNE, i.e. Compound II. The pH was maintained between 8-9.5 by addition of triethylamine, and the solution was periodically sampled over a 5-day period, to allow monitoring the reaction by thin layer chromatography. At this point the reaction of carboxyl groups of Compound II with the amino groups of Compound VII was judged complete by use of ninhydrin. The resulting solution of $(DBL)_{64}(Lys)_{63}(BHA)$ was added to 250 ml of water and washed twice with 250 ml of water. The initial precipitation was difficult to filter because of suspended materials and 7 grams of sodium chloride was added to the supernatant to flocculate the suspended materials. The mixture was filtered and the cake dried at 40° C. in vacuo and suspended in 250 ml of acetonitrile. The suspension was filtered and washed three times with 50 ml of acetonitrile. (Acetonitrile was found a more satisfactory wash medium than ether as larger molecular weights were approached because of significant solubility of the larger molecular weight product in ether). Yield: 3.78 grams (94% of theory) of $(DBL)_{64}(Lys)_{63}(BHA)$. A sample of 10 grams of the $(DBL)_{64}$ product was added to a mixture of 10 ml of methylene chloride and 30 ml of TFA, and the solution was stirred for two hours. (20% of the solution was removed for other experiments). The remaining 80% of the batch was evaporated to remove excess methylene chloride and TFA, leaving $Lys_{64}(Lys)_{63}(BHA)$ product, Compound VIII.

STAGE H—$Lys_{128}(Lys)_{127}(BHA)$=Compound IX

Compound VIII was diluted with 26 ml of DMF and adjusted to pH 8-9 with triethylamine (circa 24 ml). 32.4 grams of DBL-PNE, Compound II, was added and the reaction mixture was stirred overnight. The reaction was judged to be essentially complete on the following day but was given an extra three days of stirring. The solution was added to 1500 ml of water and washed successively with 750 ml portions of water. The precipitate was filtered and dried in vacuo at 40° C. and then extracted with 800 ml acetonitrile and then washed successively with four 800 ml portions until the wash showed no yellow color on addition of triethylamine. The precipitate was dried in vacuo at 40° C. Yield: 13.6 grams (85% of theory) of $(DBL)_{128}(Lys)_{127}(BHA)$.

A sample of 0.5 grams of the $(DBL)_{128}$ product was dissolved in a mixture of 3 ml methylene chloride and 10 ml TFA and allowed to stand for two hours until evolution of $CO_2$ was complete. The excess solvent was then evaporated leaving $Lys_{128}(Lys)_{127}(BHA)$ product, compound IX, an oil.

STAGE I—$Lys_{256}(Lys)_{255}(BHA) =$ Compound X

To Compound IX there was added 4 ml of DMF and the solution was neutralized with triethylamine to an apparent pH of 8-9; then 2.05 grams of DBL-PNE, i.e. Compound II, was added. The pH was maintained alkaline by additions of triethylamine throughout the reaction period which was continued for four days. The reaction mixture was then precipitated with 500 ml of water and washed with successive portions of water. The cake was dried in vacuo and extracted with acetonitrile. Some of the precipitate remained suspended in the acetonitrile wash; small amounts of triethylamine were added to help flocculate the material. At each stage of the wash it was necessary to centrifuge the suspension in order to get adequate recovery of product. After washing was complete, the product was dried in vacuo at 40° C. Yield: 900 mg. (90% of theory) of $(DBL)_{256}(Lys)_{127}(BHA)$. A sample of 0.5 g of the $(DBL)_{256}$ product was dissolved in 5 ml methylene chloride and 10 ml TFA and allowed to stand for two hours until evolution of $CO_2$ was complete. The excess solvent was evaporated leaving $Lys_{256}(Lys)_{127}(BHA)$ product, Compound X, an oil.

STAGE J—$(Lys_{512}(Lys)_{511}(BHA) =$ Compound XI

To Compound X there was added 4 ml of DMF. The solution was neutralized with triethylamine to an apparent pH of about 8 and 2.05 grams of DBL-PNE i.e., Compound II, was added. The pH was maintained by dropwise periodic addition of triethylamine over 4 days. The reaction mixture was precipitated with 500 ml of water and washed with two successive 200 ml portions of water. The cake was washed with successive portions of about 30 ml of acetonitrile in centrifuge tubes until the aceonitrile showed no color on addition of sodium hydroxide. In order to have the suspended materials centrifuge properly, small amounts of triethylamine were added to help by flocculating the product. After the washing was complete the product was dried in vacuo at 40° C. Yield: 630 mg. (63% of theory) of $(DBL)_{512}(Lys)_{511}(BHA)$. A sample of 1.28 g. of the $(DBL)_{512}$ product was dissolved in 12.8 ml of methylene chloride and 25.6 ml TFA and the evolution of $CO_2$ was monitored by trapping with barium hydroxide solution; the recovery of $CO_2$ was in excess of 80% of theory. The solution was then evaporated to leave an oil $Lys_{512}(Lys)_{511}(BHA) =$ Compound XI.

STAGE K—$(DBL)_{1024}(Lys)_{1023}(BHA) =$ Compound XII.

This Compound XI was dissolved in 6 ml of DMF and neutralized with about 4 ml of triethylamine. To the resulting solution was added 5.2 g. of DBL-PNE, i.e. Compound II; the solution was stirred for 4 days while maintaining the pH between 8-9 with triethylamine. At the end of this time the reaction was checked by tlc using fluorescamine as an indicator. The test was negative for free amino groups. The solution was then precipitated in 1400 ml of water, the precipitate was washed with water and dried in vacuo. The precipitate was then extracted with 400 ml of acetonitrile and washed until free of nitrophenol and nitrophenylester. Triethylamine was added during the washing to facilitate separation of the precipitate. The product was dried in vacuo at 40° C. Yield: 1.7 g. (67% of theory) of $(DBL)_{1024}(Lys)_{1023}(BHA)$, Compound XII.

It will be appreciated that at very high molecular weights, the macromolecular products designated by the formulae given above may not conform precisely to the theoretical formulae, $U = 2^n - 1$. In particular, the essentially spherical geometry of the macromolecule means that as molecular weight increases, the ratio of surface of the macromolecule: exterior units descreases; i.e., the exterior portion of the macromolecule become more crowded; the mutual interferences among the exterior units therefore increase, restricting the freedom of the exterior units to react with additional lysine molecules. However, the solubility of the product confirms that it is not cross-linked.

The amino groups of the $(DBL)_{1024}$, which attach t-butyloxycarbonyl surface units to exterior lysine units, can be liberated; and can, if desired, be further reacted with Compound II or with any other desired molecule containing a group which is reactive with amino groups thereby linking new exterior lysine units or various surface units (R) to these exterior lysine units (M). Such reactive groups include anhydride, acid halide, isocyanato, halo, and the like.

It will be recognized that, applying the same principles illustrated by the above example, macromolecules of similar structure can be formed from other diamino carboxy compounds, for example diaminopropionic acid; from dicarboxy amino compounds; and in general from trifunctional compounds having attached, to one of the two terminal carbon atoms of an alkylene hydrocarbon diradical of at least 3 carbons, the functional group A', and having attached to the other terminal carbon atom of such diradical, a different functional group B' reactive with the first group to form a linkage AB; and having attached to a third carbon in its skeleton the functional group A'' (preferably being the same as A') reactive with B', whereby a macromolecule in accordance with this invention can be built up stage by stage via consecutive reactions of groups B' with all groups A' and A'' obtained at the preceding stage. Moreover instead of a monofunctional compound such as BHA to form the "source" unit (S), a difunctional compound such as ethylene diamine can be used to link the source unit to each of two lysine molecules via their carboxyl groups; or any desired compound, monofunctional, difunctional or polyfunctional, capable of linking to the carboxyl group of lysine but inert toward its amino groups, can be used.

We claim:

1. A macromolecular compound composed of at least four successive layers of lysine units:
   the first said layer consisting of one lysine unit linked as an amide, via its carbonyl group, to an amino group of a compound (S) in which amino groups are the only groups reactive with the lysine molecule;
   the second layer consisting of two lysine units each linked as an amide, via the respective carbonyl groups, to one of the two amino groups in the lysine unit of the first layer;
   the third layer consisting of four lysine units each linked as an amide, via the respective carbonyl groups, to one of the four amino groups in the two lysine units of the second layer;
   the fourth layer consisting of eight lysine units each linked as an amide, via the respective carbonyl groups, to one of the eight amino groups in the four lysine units of the third layer.

2. Macromolecule of claim 1 wherein the compound (S) is linked to only one lysine unit.

3. Macromolecular compound of claim 2 in which the compound (S) is benzhydrylamine.

4. Macramolecular compound of claim 1 having an outermost layer consisting of surface units in each of which a carbonyl group is linked as an amide to one amino group in a lysine unit of the layer below; which surface units differ from lysine units.

5. Macromolecular compound of claim 4 wherein each surface unit is selected from the group consisting of t-butyloxycarbonyl units, phenylalanine units, tyrosine units and carboxymethyl units.

* * * * *